(12) United States Patent
Hinley, Jr.

(10) Patent No.: US 6,279,578 B1
(45) Date of Patent: Aug. 28, 2001

(54) MEDICAL DRAPE

(75) Inventor: Robert William Hinley, Jr., Spring Grove, IL (US)

(73) Assignee: Rexam Medical Packaging, Inc., Charlotte, NC (US)

( * ) Notice: Subject to any disclaimer, the term of this patent is extended or adjusted under 35 U.S.C. 154(b) by 0 days.

(21) Appl. No.: 09/232,520

(22) Filed: Jan. 19, 1999

Related U.S. Application Data

(60) Provisional application No. 60/071,863, filed on Jan. 20, 1998.

(51) Int. Cl.[7] ................................................ A61B 19/00
(52) U.S. Cl. ................................. 128/849; 128/853
(58) Field of Search ............................ 128/849–856

(56) References Cited

U.S. PATENT DOCUMENTS

| | | | |
|---|---|---|---|
| 3,668,050 | * 6/1972 | Donnelly | 128/853 |
| 3,766,913 | * 10/1973 | Balin | 128/853 |
| 3,972,328 | * 8/1976 | Chen | 128/156 |
| 4,379,192 | * 4/1983 | Wahlquist | 128/853 |
| 5,222,507 | 6/1993 | Taylor . | |
| 5,546,960 | 8/1996 | Billgren . | |
| 5,698,294 | 12/1997 | Van Hout et al. . | |

FOREIGN PATENT DOCUMENTS

| | | |
|---|---|---|
| 0560630A1 | 3/1993 | (EP) . |
| WO 94/01051 | 1/1994 | (WO) . |
| WO 96/09165 | 3/1996 | (WO) . |
| WO 96/25907 | 8/1996 | (WO) . |

* cited by examiner

*Primary Examiner*—Michael A. Brown
(74) *Attorney, Agent, or Firm*—Alston & Bird LLP

(57) ABSTRACT

A medical drape for retaining and controlling fluid flow comprising at least one polymeric film having a predetermined texture made from a plurality of cells able to retain fluid.

6 Claims, 7 Drawing Sheets

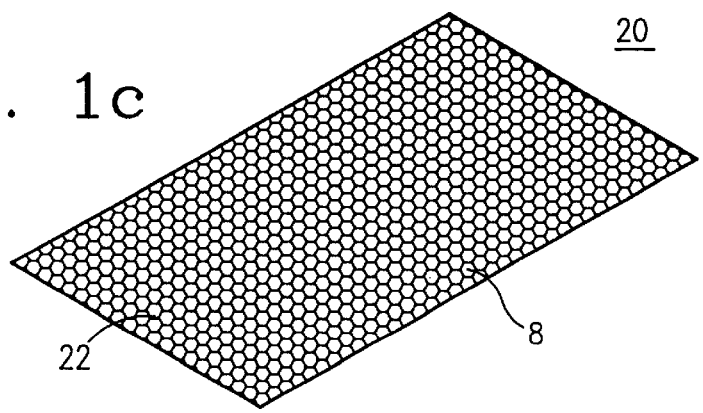
FIG. 1c
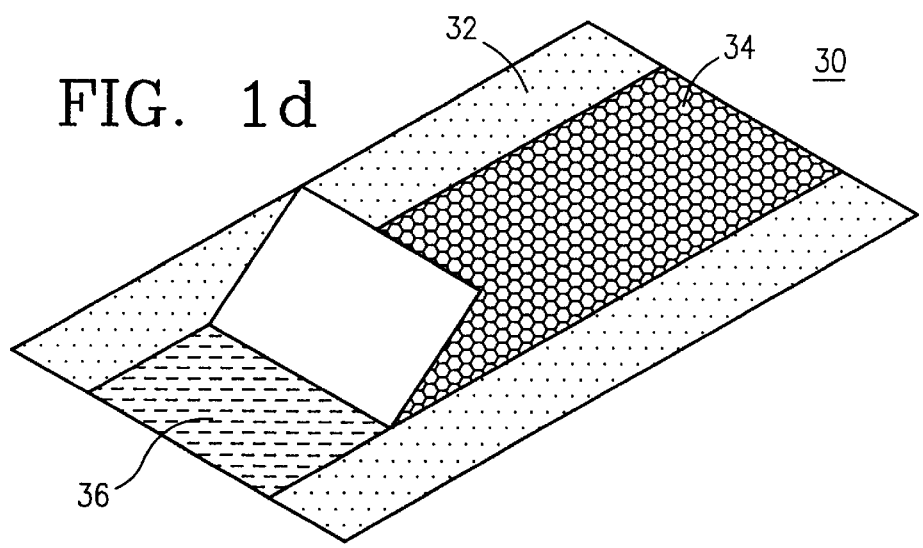
FIG. 1d
FIG. 2
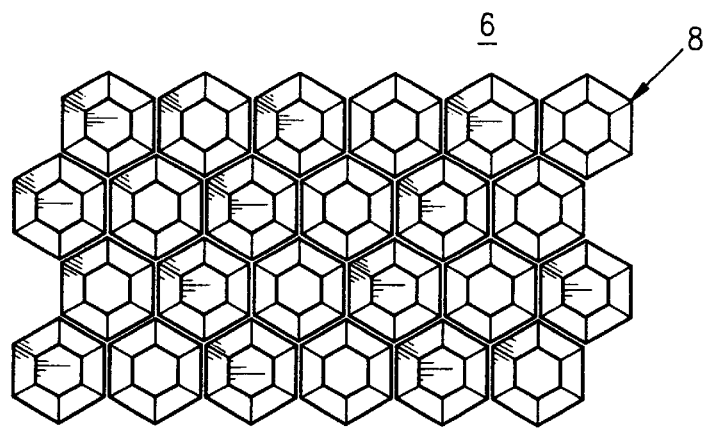

MEDICAL DRAPE

CROSS-REFERENCE TO RELATED APPLICATIONS

This application claims the benefit of U.S. Provisional Application No. 60/071,863, filed Jan. 20, 1998.

FIELD OF THE INVENTION

The present invention relates to sterilizable drapes used in the medical field, and more particularly sterilizable drapes used as back table covers and Mayo stand covers. More specifically the present invention relates to sterilizable back table covers that have integrated fluid containment sections.

BACKGROUND OF THE INVENTION

Surgical drapes are commonly used in the medical field. Such drapes commonly are used to cover the patient during medical procedures, exposing to the doctors and nurses only areas of the patient requiring attention. In the medical environment, it is also important to cover areas and stations where health care workers work and retrieve instruments. Back tables and Mayo stands also commonly receive such covers. Conventional drapes comprise non-woven materials, or non-wovens attached to plastic sheets. The table cover functions as a sterile surface to support medical devices and supplies. During procedures condensation may form on packages or devices that have been sterilized,(e.g. autoclaved). Such condensation can collect on the table cover as the device or package cools. In addition, instruments or other devices and dressings become coated with various fluids (e.g. blood, lymph, saline, etc.). Such fluids can collect on the Mayo stand cover. Conventional non-woven sections of the table covers absorb and otherwise contain such fluids.

In addition, it is desirable to present instruments and supplies in the operating room using sterile technique, whereby instrument kits comprise sterilized instruments that are opened and uncovered while simultaneously providing a table cover to a table or other support surface. In this way, the package for the instruments is unfolded carefully to provide a sterile surface on which the instruments contained therein may be placed. The instruments are then ready for use by medical personnel. Such packages and table covers must not lint; that is, they must not be susceptible to small fibers coming loose therefrom, since such loose fibers resulting from materials that "lint" can find their way into open wounds and otherwise compromise a sterile environment.

Further, drapes and table covers in the medical field must unfold to drape flat into their final positions without requiring additional positioning and adjustment. This is because such additional handling compromises the sterile field. Therefore, a useful drape or table cover will have sufficient weight or heft to stay in place once positioned and will not require any additional "smoothing out".

Therefore, a non-linting back table cover to support medical instruments and devices, and that is also capable of providing superior fluid containment and control, while being sterilizable and cost-effective to manufacture, would be advantageous.

SUMMARY OF THE INVENTION

According to the present invention, one preferred embodiment relates to a polymeric film for enhancing fluid control and retention comprising a predetermined pattern of cells. In another preferred embodiment, the polymeric film has a first section having a first texture and a second section having a second texture different from the first texture, said second texture being a predetermined pattern of cells to enhance fluid control and retention. Further, the second section may have more than one predetermined pattern of cells.

In a further embodiment, the present invention relates to a medical drape comprising a first polymeric film having a first texture comprising a predetermined pattern of cells. The invention further contemplates a medical drape having a first polymeric film having a first texture and a second polymeric film having a second texture. The second texture has a predetermined pattern of cells.

Still further, the present invention, in another embodiment contemplates a sterilizable medical drape having two layers comprising a first polymeric sheet having a first dimension and a second polymeric sheet having a dimension smaller that the first dimension. The second sheet is affixed to the first sheet.

In a still further embodiment the present invention contemplates a method for retaining fluid on a medical drape comprising the steps of providing a polymeric film having at least one layer having a predetermined pattern of fluid-retaining cells, providing an amount of fluid to the film, and retaining the fluid in the cells.

In a further embodiment, the present invention contemplates a method for retaining fluid on a medical drape comprising providing a first sheet and a second sheet and adhering the sheets together. The second sheet comprises cells for retaining fluid, and may be treated to improve hydrophilicity.

The present invention therefore relates to a plastic sheet material that has improved fluid retention characteristics. The present invention also relates to a sheet material made from the preferred formulation which has its surface textured into a predetermined pattern to enhance fluid control and retention. Further, the present invention relates to a drape such as a back table and Mayo stand cover having a central section made from a polymeric sheet material having predetermined surface textured pattern specially formulated and textured to improve fluid control and retention. In another preferred embodiment, the present invention relates to a back table cover having discrete zones made from differing polymeric sheet materials with the central portion covering the table surface and specially textured and formulated to have superior fluid control and retention.

The present invention also relates to a medical drape or cover having the textured characteristics already described above, but made from one material, wherein either all or portions of the surface are textured.

A more complete understanding of the invention can be had by reference to the following detailed description and the attached drawings.

BRIEF DESCRIPTION OF THE DRAWINGS

FIG. 1c is a perspective view of a back table cover made from a single sheet and having one textured field.

FIG. 1d is a perspective view of a back table cover having a secondary field sheet laminated to a primary field sheet.

FIG. 2 is an enlarged view of the textured pattern on the central portion of the back table cover.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1A:
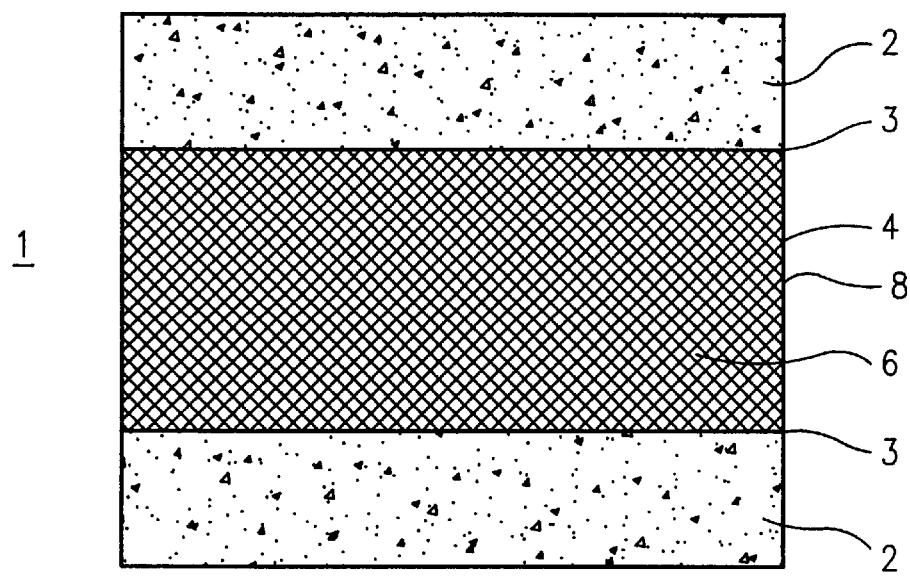
FIG. 1a is a plan view of the back table cover of the present invention.

FIG. 1a shows a perspective view of a back table cover 1 having a primary field (side sheet sections) 2 to which is attached a secondary field (central sheet section) 4 at secondary sheet edge boundaries 3. A textured surface area 6 on the secondary field is evident. The secondary field is joined to the primary field via adhesive located at the boundary 3 or elsewhere between the sheet layers. It is understood that the medical drapes of the present invention may be made from one sheet of material. Such a sheet may have one or more textured areas to retain fluids. Each zone may comprise a single texture, or may comprise a plurality of textures some or all of which may be cell-containing areas. For example, the use of multiple zones of predetermined and varying textures could enable a design or logo to be embossed into the sheet. One preferred cover is shown in FIG. 1d. In this figure, the secondary field sheet 34 is adhered to the primary sheet 32 via an adhesive layer 36 to make the finished product 30. The layer 36 has a dimension about equal to the secondary field sheet 34.

Figure 1B:
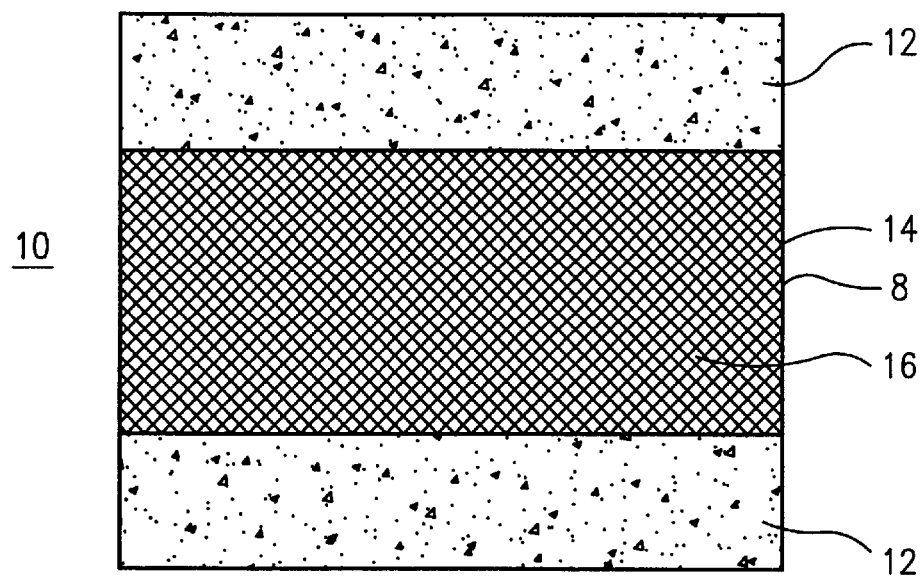
FIG. 1b is a plan view of a back tray table cover made from a single sheet and having two textured fields.

In one embodiment of the present invention, as shown in FIG. 1b, the cover 10 comprises a secondary field 14 coextruded with the primary field 12 such that the two fields are joined thermally into one sheet 10. FIG. 1c shows a sheet 20 having one textured field 22 that encompasses the entire surface area of the cover 20.

It is further understood that the primary sheet may itself comprise a two sheet laminate having, for example, a top sheet having a first color and a bottom sheet having a second color different from the first color. The two sheets comprising the primary sheet may be laminated together or coextruded.

Figure 3:
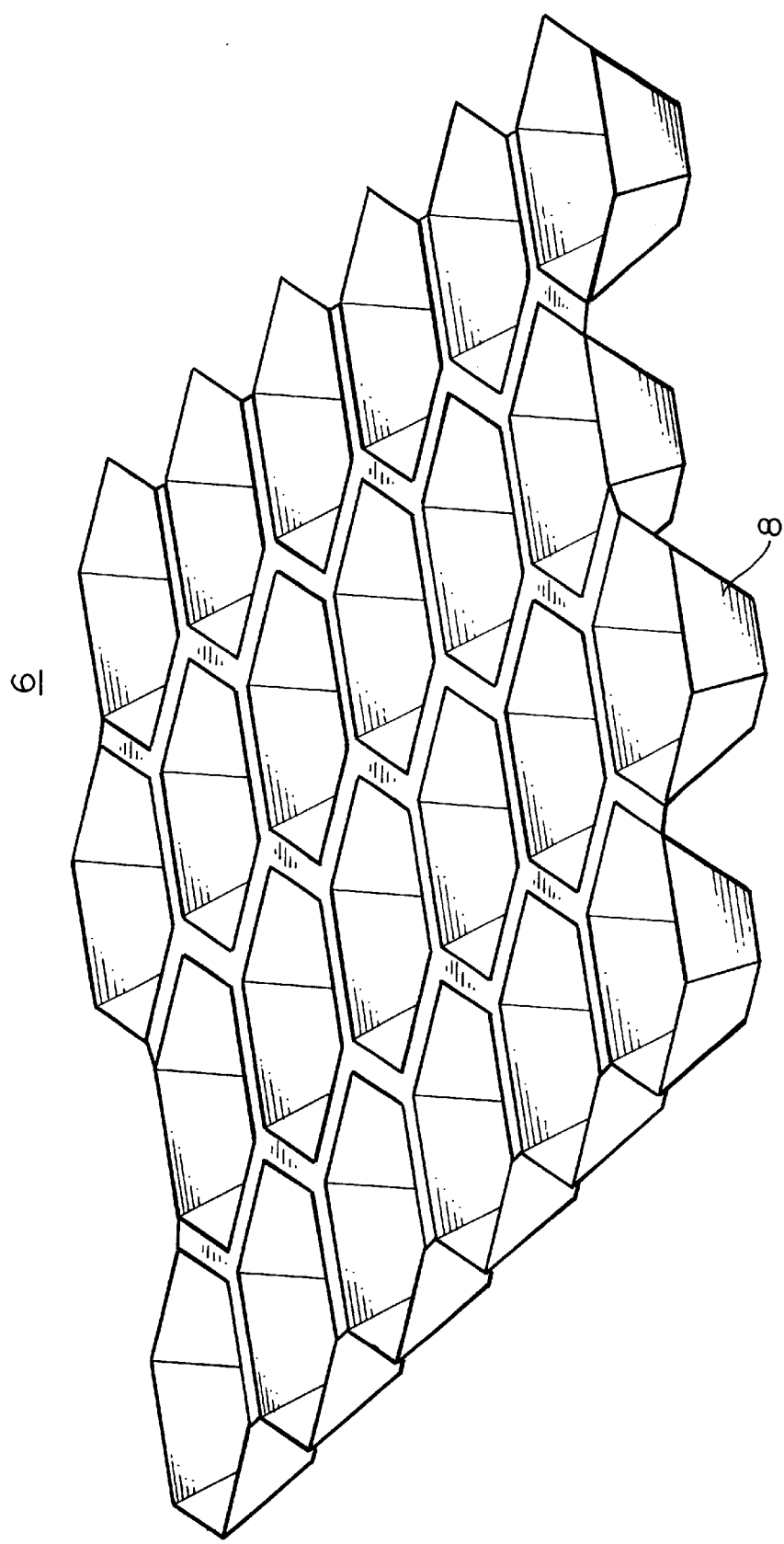
FIG. 3 is a further enlarged perspective view of the textured pattern shown in FIG. 2.

FIG. 2 shows an enlarged view of the cells 8 of the textured surface area 6. FIG. 3 is a further enlarged perspective view of the cells 8 of textured surface area 6 of secondary field 4. The depth of the cells 8 is clearly visible.

The secondary field is a replacement and significant improvement for the non-woven materials commonly used as the secondary field for known back table covers. The secondary field of the present invention is made from a polymeric material such as polyolefins, polyamides, polyesters and ionomers. Preferably, the secondary field or sheet is a polymeric material such as a high density polyethylene (HDPE), polypropylene, a plastomer, a linear low density polyethylene (LLDPE), an ultra linear low density polyethylene (ULLDPE) or combinations thereof. The secondary field is most preferably a heat resistant polyolefin sheet material that can be fashioned into a predetermined surface textured pattern with cup-like shaped cells or depressions being most preferred.

Preferred formulations for the secondary field comprise from about 50 to about 90% HDPE; from about 0 to about 40% plastomer; from about 5 to about 30% polymeric pigmenting agent; and from about 5 to about 15% surfactant such as wetting agent. Most preferred is a polymeric blend comprising about 76% HDPE (Chevron 9638); about 10% plastomer (Exxon 3132); about 6% Techmer surfactant (RMN 114224E4); and about 8% Ampacet blue. All percentages are based on weight %.

When a second sheet is adhered to a first or primary sheet, the primary sheet preferably is made from a film material such as low density polyethylene (LDPE), linear low density polyethylene (LLDPE), ultralinear low density polyethylene (ULLDPE), plastomers and combinations thereof. Preferably the primary sheet comprises a polymeric blend of from about 60 to about 90% LLDPE; from about 0 to about 40% ULLDPE; from about 0 to about 40% plastomer; and from about 5 to about 10% pigment.

Figure 4:
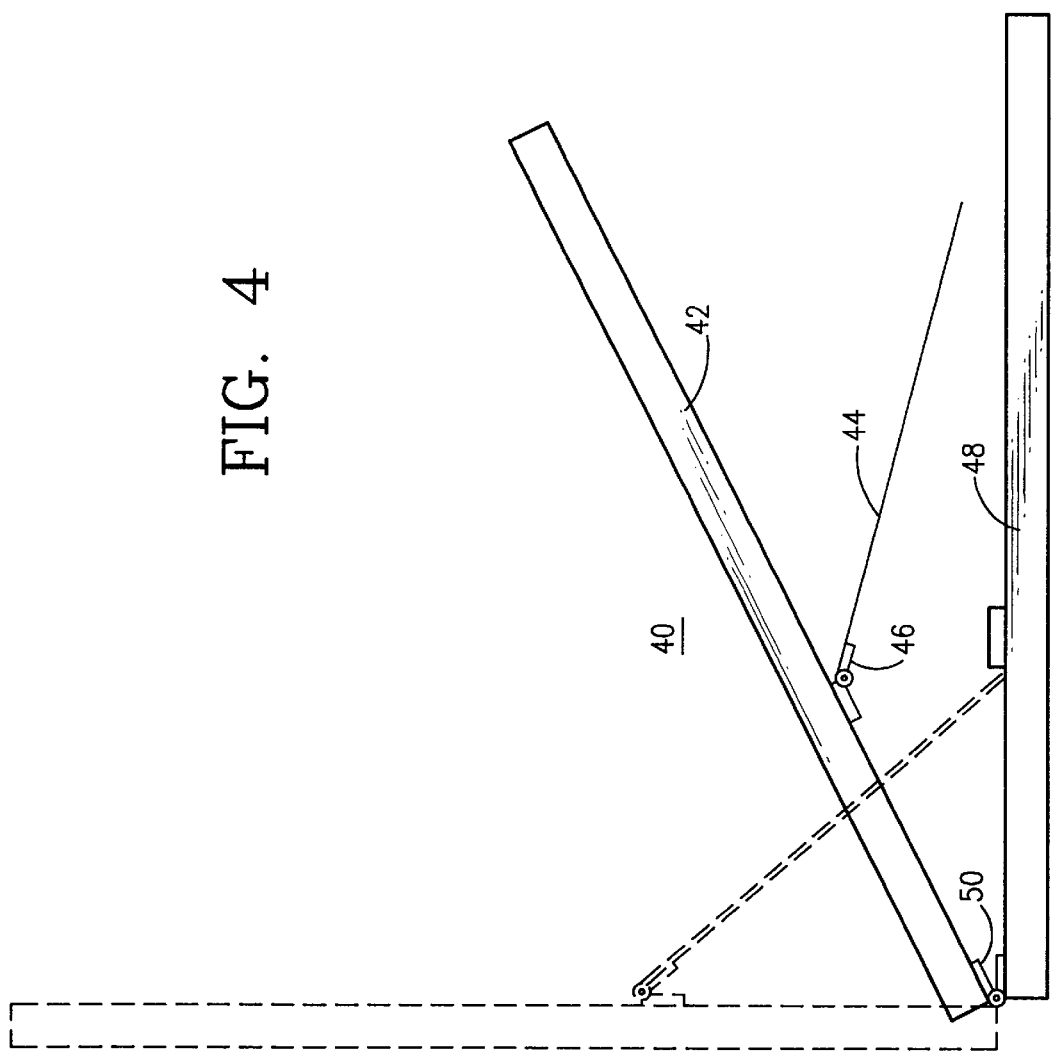
FIG. 4 is a side view of the inclinometer testing apparatus used to measure fluid retention and containment.

FIG. 4 is a side view of the inclinometer testing apparatus used to measure fluid retention and containment and discussed further in Example 1.

The embossed sheet or drape (which may be the first, or second sheet or both) has a pattern of cells embossed into its surface creating regular or random patterns of a predetermined depth, as desired. The depth of each geometric depression or cell contributes to the degree that liquid is captured therein, thereby reducing fluid migration across its surface. The cells preferably have a water holding or capture capacity of from about 0.05 $g/in^2$ to about 0.31 $g/in^2$, most preferably at least about 0.10 $g/in^2$. In many instances, the cell-containing sheets and drapes of the present invention can capture and retain in excess of about three times the weight of the drape itself. In one preferred embodiment of the present invention, the secondary field of the cell-containing drape produced as a two sheet laminate captures and retained an amount of water up to about 3.68 times the secondary field weight. When the present invention is coextruded, the secondary field of the drape retained an amount of water up to about 2.86 times the secondary field weight.

As mentioned above, the cells may have preferred geometric orientations or groupings. The cell shape can have any desired configuration, with the cell walls and cell base being flat or curved so long as desired fluid capture and retention is achieved. Further the walls may be perpendicular or angled with respect to the base (floor) of the cell. The cell floor may be smooth or textured or itself may have features such as ridges, roughness, etc. that assist in fluid capture and retention. In addition, the cell base may have a diameter less than or greater than the top or opening of the cell, resulting in angled cell walls. The cell pattern can be formed using any forming methods including embossing, thermoforming, pressure forming, molding or other methods.

The cells preferably are hexagonal having linear floors and walls, commonly referred to as a "hex pin" design. This design is shown in detail in FIGS. 2 and 3. The choice of radiused (i.e. rounded cell bottom or cup-like shape) or non-radiused (i.e. straight-walled hexagonal) cells will affect the general appearance of the sheet. The non-radiused cells tend to diffract incoming light in such a way as to achieve a dull or less reflective looking surface as compared to the surface achieved through the use of radiused cells. The cells may be embossed into the sheet to any desired configuration and to any desired depth. When the sheets are employed as medical drapes, the preferred embossed films or sheets of the present invention have cell depths of from about 8 mils to about 16 mils, and are preferably about 14 mils deep.

Deeper cells can be achieved, but considerations such as bulk and product "feel" must be taken into account. According to the present invention, drapes having superior fluid retention have been made having from about 225 to about 325 cells/in$^2$, with the preferred sheets having from about 290 to about 315 cells/in$^2$. One particularly preferred embodiment results in an embossed pattern of about 310 cells/in$^2$.

If a two sheet construction is desired, such as for a Mayo stand or back table cover, the sheet for the secondary field is also preferably formulated to have enhanced wettability beyond that which can be accomplished through conventional flame or corona treatment. For the purpose of the present invention, wettability is understood to be a property that can be measured by surface energy. A high surface energy material, is more wettable than a low surface energy material. "Hydrophilicity" is under stood to be the extent to which a material has an affinity for water. The wettability and hydrophilicity of the films of the present invention can also be enhanced by applying surfactants to the sheet surface. Surfactants are understood to be compounds that enhance wettability and which may be applied topically either to a film surface or may be incorporated into the sheet formulations. These incorporated surfactants then migrate to the sheet surface after fabrication and improve hydrophilicity. Surfactants able to increase hydrophilicity and liquid retention are most preferred as would be readily understood by one skilled in the field of surfactants and film treatment and manufacture.

The textured sheet for the secondary field may be joined to the first sheet (primary field) material by any acceptable method such as adhering, heat sealing etc. In one embodiment, the secondary field is coextruded with the first sheet material to create the hybrid material containing outer primary field or side sections made from the first material, and the secondary or central field textured section made from, for example, the preferred polyolefin textured sheet material. If adhesive sealing is desired, the preferred adhesive preferably is a pressure sensitive water based, hot melt based or solvent based adhesive. Whatever, adhering method is selected must result in a multi-sheet product that is heat, chemical vapor (e.g. ethylene oxide) or radiation (gamma) sterilizable. The drapes of the present invention may also be components of other products such as trays or kits.

It is contemplated that the textured sheet material of the present invention may represent the entire material used to make the tray cover (i.e., a sheet of only one material is used which is textured throughout, or at least over a portion thereof). However, cost and other manufacturing constraints may dictate the need to use the hybrid material.

The present invention exhibits many advantages over known back table covers used in the medical profession. The covers of the present invention are physically stronger since they are made from a polymeric as opposed to the non-woven materials commonly used, such as GR11551 sold by Dexter Corp.(Windsor Locks, Conn.). The textured cell-containing pattern in the preferred polymeric sheets of the present invention also offers enhanced cushioning for the instruments laid thereon as opposed to the non-woven material. Most importantly, the patterned and textured surface of the sheet material of the present invention affords improved fluid capture and containment as compared with many currently available materials.

The preferred material of the present invention can also be manufactured with greater variety of appearance and therefore can more completely satisfy consumer demand from an aesthetic standpoint. For example, the textured cell design of the present invention can be embossed into the polymeric sheet in the configuration of a logo. By contrast, in conventional table covers, non-wovens have a look that is more cloth-like, and which can't be textured into a pattern.

Still further, the textured sheet of the present invention can be made to complement the first sheet material in terms of recyclability such that the entire table cover can be easily recycled as one unit. Presently, to recycle back table covers having non-woven central segments, the central non-woven segment must first be removed and discarded as a separate cost-adding step.

In addition, the sheets of the present invention are more easily manufactured and assembled than are the non-wovens currently in use. For example, if the two plastic materials are to glued together, adhesive bleeding through the material is not a concern as it is when assembling non-wovens via gluing to polymer side sheets. As already mentioned, if the product of the present invention is to be made from two or more materials, the materials can be coextruded or produced as a laminate with the secondary field (central section).

Figure 6:
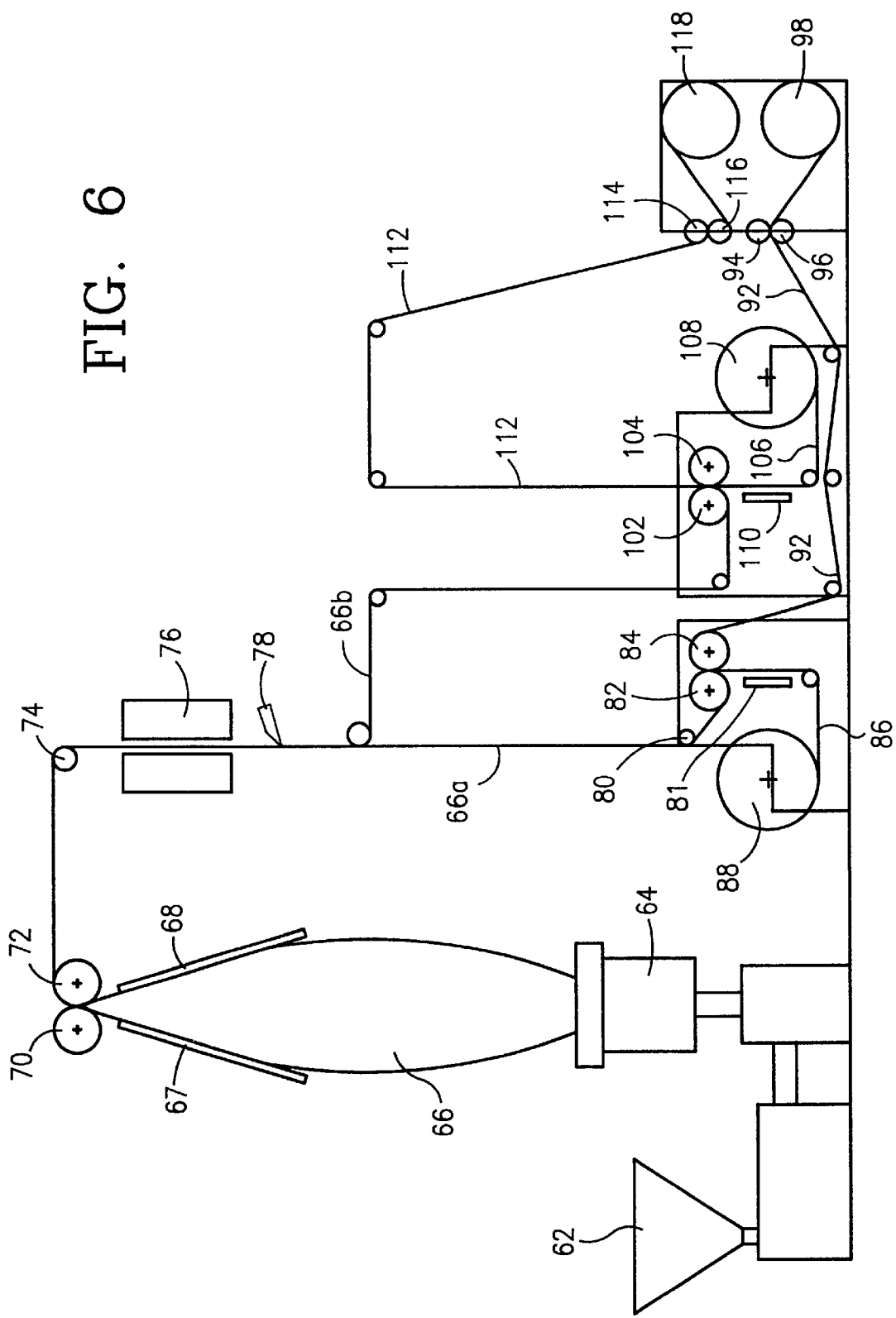
FIG. 6 is a schematic side view of the manufacturing laminating line for one embodiment of the present invention.

FIG. 6 shows a schematic representation of a lamination line process to make the laminated product of the present invention. Raw material is delivered to the extruder and die 62. The primary film 66 is extruded and blown through the blown film die 64. The primary film is directed against guides 67, 68 and drawn through nip rollers 70, 72. The primary film then proceeds past a corona treatment 76 about roller 74 and past edge slitting station 78 and slit to desired width. Film 66 is thus split into films 66a and 66b. Film 66a proceeds about directional roller 80 to embossing rollers 82, 84. Secondary film 86 is supplied from roll 88 and directed through adhesive application station 81 and embossing rollers 82, 84. Primary film 66a and secondary film 86 are joined in the embossing rollers and the product film 92 is drawn through tension rollers 94, 96 and wound onto roller 98. Meanwhile, film 66b is directed to embossing rollers 102, 104. Secondary film 106 is delivered from roll 108 to adhesive station 100 where adhesive is applied. Secondary film 106 and primary film 66b join at the embossing rollers 102, 104 to make product film 112. Film 112 is drawn through tension rollers 114, 116 and wound upon roller 118.

Figure 7:
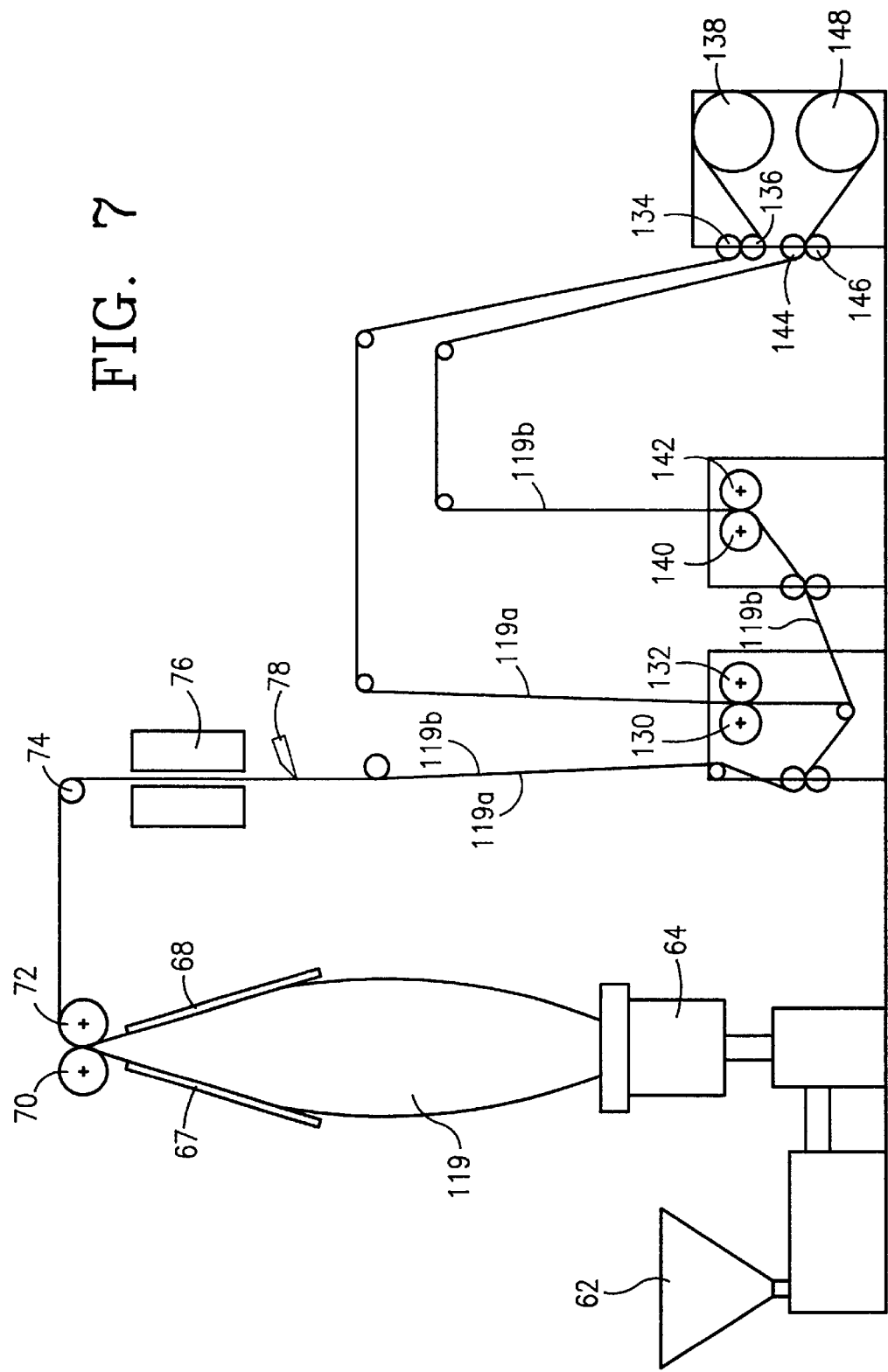
FIG. 7 is a schematic side view of the manufacturing coextrusion line for one embodiment of the present invention.

FIG. 7 shows a schematic representation of a coextrusion line process to make the coextruded product of the present invention. Film 119 is extruded, blown, corona treated and edge slit as in the lamination process of FIG. 6. The film is then directed to poly film embossers 130, 132. Film 119 comprises a two or three layer extrusion die 64. Film 119 is then separated into films 119a and 119b. Film 119a is directed to embosser rollers 130, 132, tension rollers 134, 136 and winder roll 138. Film 119b is directed to embossing rollers 140, 142 and onto tension rollers 144, 146 and onto winder roll 148.

The following examples serve only to further illustrate aspects of the present invention and should not be construed as limiting this invention.

EXAMPLE 1

Rexam Fluid Containment Test

A fluid containment test was conducted for several samples. The Rexam fluid containment test was developed to determine the distance a fluid travels or is retained on a substrate. The material to be tested is secured to a testing platform. The testing platform comprises a 4"×24" ramp attached to a support and a base. The three part apparatus is 40 shown in FIG. 4. The apparatus 40 is preferably made from plexiglass, but it is understood that the apparatus may be made from any suitable material. As shown in FIG. 4, the ramp 42 is secured to the support 44 with hinge 46. Base 48, is secured to the ramp 42 with hinge 50. According to the testing method protocol, a sample material is cut into a 4"×24" section and placed on top of the ramp section. The top and bottom of the sample are secured, preferably via tape to the ramp. The sample must remain flat and entirely adjacent the ramp. The ramp is initially set in the horizontal or 180 degree position. An eye dropper is filled with distilled water at room temperature. Three drops of distilled water (room temperature) are placed at one end of the sample. The ramp is slowly raised to a position perpendicular to the base, at an angle of approximate 90 degrees, until the fluid begins to travel down the sample. The distance the fluid travels (and possibly stops) is also recorded. Multiple runs are made to gain a representative sampling.

EXAMPLE 2

Fluid Containment Test Results

Figure 5:
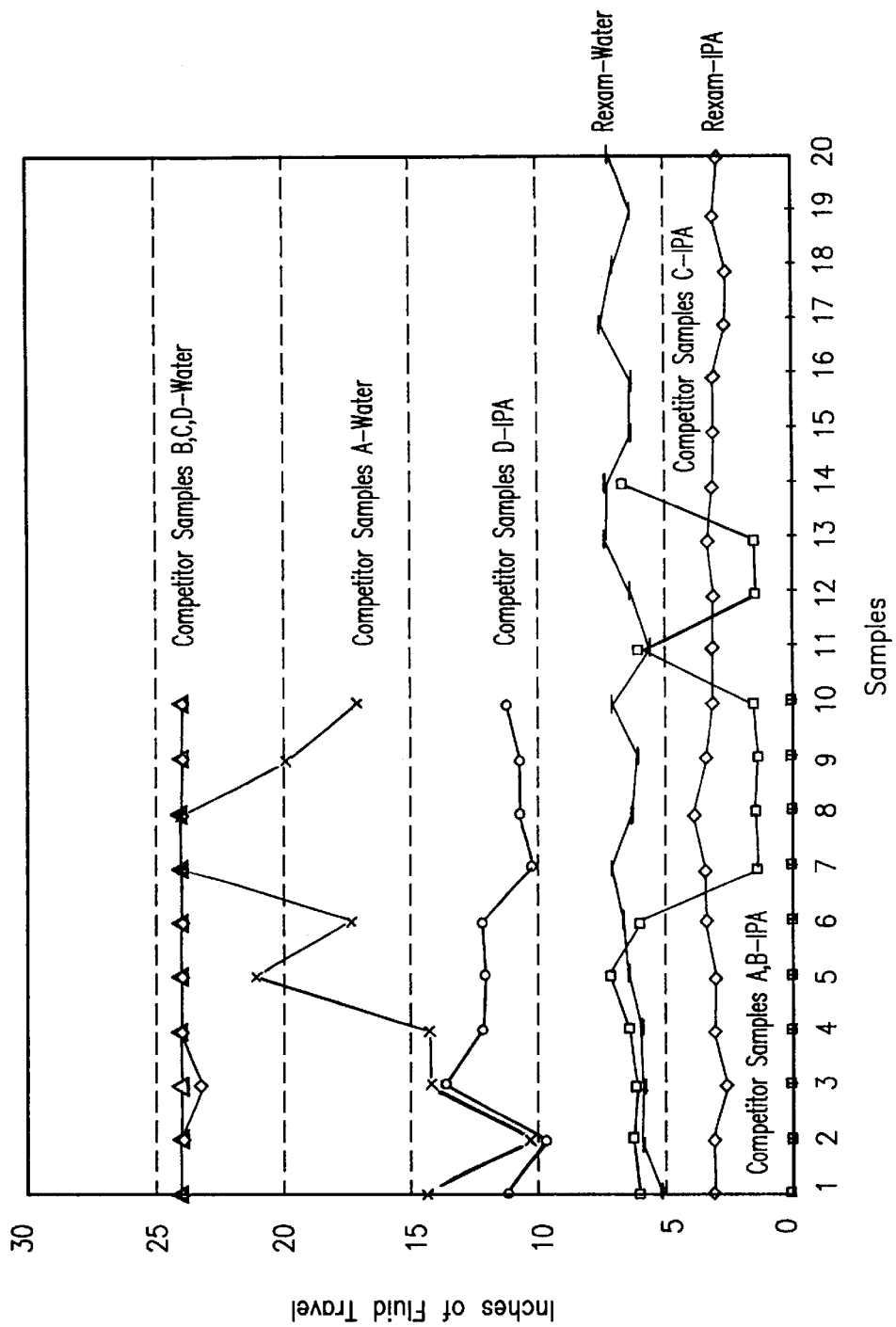
FIG. 5 is a chart showing the plotted data point obtained from fluid containment test runs.

Competitive material samples were evaluated according to the protocol of Example 1. Competitive samples A, B, C and D and samples of the present invention were tested using both water and isopropyl alcohol (IPA). At least ten runs were made for each sample. The runs were plotted and are presented in FIG. 5. Each of the competitive samples A, B, C and D for water and sample D for IPA showed higher inches of fluid travel than did the tested samples of the present invention. Competitive sample C for IPA showed mixed results with about half of the test runs showing results comparable to the present invention tested with IPA.

The foregoing are but examples of the variations that are envisioned as being within the spirit of the invention. Many other modifications and variations of the present invention are possible to the skilled practitioner in the field in light of the teachings herein and therefore the present invention may be practiced other than as described herein.

What is claimed:

1. A medical drape comprising a first polymeric film having a first texture and a second polymeric film having a second fluid-retaining texture, said second texture being a pattern of cells having a predetermined volume and geometric configuration, and a depth of from about 8 mils to about 16 mils.

2. The drape according to claim 1, wherein the cell depth is about 14 mils.

3. A medical drape comprising:
a first polymeric film having a first texture and a second polymeric film having a second fluid-retaining texture, said second texture being a predetermined pattern of cells arranged in a pattern of from about 225 to about 325 cells/in$^2$.

4. The drape according to claim 3, wherein the second film comprises about 310 cell/in$^2$.

5. The drape according to claim 3, wherein the second film retains an amount of fluid equal to from about 0.05 g/in$^2$ to about 0.31 g/in$^2$.

6. A medical drape comprising a first polymeric film having a first texture and a second polymeric film having a second texture being a predetermined pattern of fluid retaining cells, said cells having a predetermined volume and geometric configuration, wherein the second film further comprises surfactants.

* * * * *